United States Patent [19]

Cook et al.

[11] 4,290,911

[45] Sep. 22, 1981

[54] AGAROSE COMPOSITION, AQUEOUS GEL AND METHOD OF MAKING SAME

[75] Inventors: Richard B. Cook, Rockland; Henry J. Witt, Rockport, both of Me.

[73] Assignee: FMC Corporation, Philadelphia, Pa.

[21] Appl. No.: 10,033

[22] Filed: Feb. 7, 1979

[51] Int. Cl.³ .................... B01J 13/00; B01D 57/02
[52] U.S. Cl. .................. 252/316; 204/180 G; 252/408
[58] Field of Search ............... 252/316, 408; 204/180 G; 106/205, 208; 536/114

[56] References Cited

U.S. PATENT DOCUMENTS

| | | | |
|---|---|---|---|
| 2,466,146 | 4/1949 | Baker | 252/316 X |
| 2,508,726 | 5/1950 | Ramstad et al. | 536/114 |
| 3,527,712 | 9/1970 | Renn et al. | 252/316 |
| 3,767,787 | 10/1973 | Segal | 252/316 X |
| 3,783,118 | 1/1974 | Hjerten | 204/180 G |
| 4,146,454 | 3/1979 | Haber | 204/180 G X |

OTHER PUBLICATIONS

Johansson et al.: "Electrophoresis, Crossed Immunoelectrophoresis, and Isoelectric Focusing . . . ", Anal. Biochem., vol. 59, pp. 200–213 (1974).
Quast: "The Electroosmotic Flow in Agarose Gels . . . ", J. Chromat., vol. 54, pp. 405–412 (1971).
Weise et al.: Progress in Isoelectric Focusing and Isotachophoresis, Ed. Righetti, North Holland Publ. Co., 1975, pp. 93–98.
Saravis: Abstract Entitled Immunoelectrophoresis Publ. in Conjunction with 1978 Electrophoresis Conference, Apr. 19–21, 1978.

*Primary Examiner*—Richard D. Lovering
*Attorney, Agent, or Firm*—Charles H. Johnson; Eugene G. Horsky

[57] ABSTRACT

A finely-divided solid blend of (1) purified agarose having an electroendosmosis value ($-Mr$) below 0.10 with (2) a water-soluble gum which by itself is soluble in boiling water without gelling, free from charged groups and from electroendosmosis, and soluble in water to form a solution of gum having at a concentration no greater than 10% by weight a viscosity of at least 10 cps. at 25° C. The blend is soluble in water to form a gel having no electroendosmosis and useful as a medium for carrying out isoelectric focusing.

8 Claims, No Drawings

AGAROSE COMPOSITION, AQUEOUS GEL AND METHOD OF MAKING SAME

This invention relates to a finely-divided solid blend of purified agarose with a gum free from charged groups and which forms a high viscosity solution in boiling water without gelling, the blend being soluble in water to form a gel having no electroendosmosis ($-Mr$), and to the aqueous gel and to the method of using it as a medium for conducting isoelectric focusing.

It has previously been proposed to employ aqueous gels made from agarose as a medium in which to carry out isoelectric focusing. However, in order to achieve satisfactory isoelectric focusing, it is essential that the gel medium have extremely low electroendosmosis properties, as close to zero as possible. Despite many efforts to purify agarose by removal of the ionic or charged groups (such as sulfate and/or carboxylate) which cause electroendosmosis in such a gel, it has not been possible as a practical matter to remove all of the groups causing electroendosmosis, as a result of which even gels made from highly purified agarose display appreciable electroendosmosis values ($-Mr$), of the order of 0.02 or more. The magnitude of this value, although slight compared to the usual value for unpurified agarose, is sufficiently high to preclude successful widespread use of agarose gels as a medium for isoelectric focusing. It has consequently been attempted to reduce the electroendosmosis of agarose gels still further by mixing with the agarose a variety of water-soluble materials supposedly free from ionic groups, such as sucrose (Quast, J. Chromat., Vol. 54, page 405–412, 1971), polyethylene oxide (M.W. 4,000,000) or polyacrylamide (Johansson et al., Anal. Biochem., Vol. 59, pages 200–213, 1974), and methyl cellulose (Weise et al., Progress in Isoelectric Focusing and Isotachophoresis, Ed. Righetti, North-Holland Publishing Co., 1975, pages 93–98). However, the first material, sucrose has little or no effect in reducing the electroendosmosis value of agarose gel. The addition of commercially available polyacrylamide, on the other hand, has an adverse effect on gels of highly purified agarose since it itself displays measurable electroendosmosis in aqueous gel form and since it tends to hydrolyze at various pH levels, leading to the formation of carboxylate groups and a still further increase in electroendosmosis. So far as polyethylene oxide (M.W. 4,000,000) and methyl cellulose are concerned, aqueous solutions of these materials gel upon heating to temperatures approaching the boiling point; whereas agarose dissolves in water only at elevated temperatures, preferably at the boiling point. A blend of either of these two dry solid materials with agarose consequently cannot be dissolved in water, and it is possible to prepare a solution containing both agarose and one of the other materials only by dissolving them separately with careful control of temperature.

It has also been proposed in Renn et al. U.S. Pat. No. 3,527,712 to prepare dry solid agarose in rehydratable form by incorporating in it a certain kind of macromolecular hydrocolloid; neither the agarose nor the hydrocolloid is required to have any specified extent of purity, and many of the hydrocolloids disclosed as suitable contain charged or ionic groups which produce electroendosmosis. Two of the hydrocolloids disclosed are low molecular weight polyethylene oxides; 10% by weight solutions of these in water have viscosities far below 10 cps. at 25° C.; and they are ineffective in reducing the electroendosmosis value of agarose. Although guar gum, a non-ionic material, is disclosed as a hydrocolloid, neither clarified guar gum nor clarified locust bean gum which are needed for use in the present invention, are mentioned. Unclarified guar gum and unclarified locust bean gum contain hull fragments and other impurities which obscure or intereferewith staining, used in isoelectric focusing procedures.

It has now been found that a dry solid blend, preferably in finely-divided form, of (1) purified agarose having an electroendosmosis ($-Mr$) value no greater than 0.10 with (2) a water-soluble gum free from hull fragments, free from ionic substituent i.e. charged groups, soluble by itself in water without gelling at temperatures up to and including the boiling point (100° C. at 760 mm. (Hg)) to form a viscous solution having a viscosity at a concentration no greater than 10% by weight of at least 10 cps. at 25° C., is useful in making aqueous gels having greatly reduced or no measurable electroendosmosis value over a wide range of pH values. Such gels are of great value for use as a medium in which to carry out isoelectric focusing of proteins.

The agarose employed in the blend can be any which has been sufficiently purified so that it exhibits an electroendosmosis value ($-Mr$) of 0.10 or less, several of which are now commercially available. Agarose having this degree of purity differs from agarose previously generally available in that such purified products display no increase in gel strength when in admixture with locust bean gum or clarified locust bean gum, whereas agarose of a lesser degree of purity (having a $-Mr$ value greater than 0.10) does exhibit such an increase in gel strength, as described for example in Baker U.S. Pat. No. 2,466,146. The electroendosmosis value of the impure agarose cannot be eliminated or decreased to zero by blending with it a water-soluble high viscosity gum as can be that of the purified agarose.

The electroendosmosis value of the agarose is measured by preparing a 1% by weight solution of the agarose in 0.05 M pH 8.6 barbital buffer. Three milliliters of the solution is poured on a clean microscope slide and allowed to gel at room temperature. Using a squared off No. 13 needle attached to a hypodermic syringe, a single hole is aspirated from the center of the gel. A standard test solution is prepared which consists of 10 mg/ml Dextran 500 (Pharmacia) and 2 mg/ml crystalline (4×) human albumin in 0.05 M pH 8.6 barbital buffer. Using a small bore dropper, sufficient solution is added to nearly fill the aspirated hole. These slides are then placed in position for electrophoresis using paper wicks. A potential of 10 volts/cm (75 volts) is applied using constant voltage settings.

Electrophoresis is continued for three hours, then the slides removed. Visualization is accomplished in two stages. The slides are first place in denatured (3A) ethanol for 15 minutes after which time the position of the dextran can be measured with respect to the origin (center to center). After measuring, the slides are transferred to protein staining solution prepared from 0.5 g amido black in 50 ml glacial acetic acid, then made up to 500 ml with ethanol. After 15 minutes the slides are washed in a 1:1 HoAc (5%):EtOH solution to remove excess stain. An hour is sufficient although the albumin position can usually be determined after 15 minutes. The distance from the center of the spot to the center of the origin is measured.

Diagramatically this can be represented as:

⊕A    O    D⊖

A=albumin, O=application point (origin), D=dextran

The degree of electroendosmosis (Mr) can be calculated using the equation:

$$-Mr = (OD/AO + OD).$$

The gel strengths (also known as "breaking strengths") referred to herein can be measured by using the procedure and apparatus described in Foster et al. U.S Pat. No. 3,342,612 granted Sept. 19, 1967, the description of which is incorporated herein by reference and by providing an automatic drive to advance the plunger at a constant rate of 16.83 cm/min. Gelation is accomplished for purpose of the test by cooling the solution at 5°–10° C. for 24 hours, and the measurement is made at 25° C. using a plunger having a diameter of one centimeter.

Any of a variety of known purification procedures including fractional precipitation, solid phase adsorption of impurities as in ion-exchange chromatography and the like can be used either alone or in combination with each other to decrease the sulfate and/or carboxylate content of the agarose and to decrease its electroendosmosis value.

The water-soluble gum must be one which by itself dissolves in water at temperatures up to the boiling point without gelling; the gum must form by itself a solution of appreciable viscosity, i.e., a solution which at a concentration no greater than 10% of the gum by weight displays a viscosity of at least 10 cps. at 25° C. Some suitable water-soluble gums form solutions of this viscosity at low concentration, of the order of 0.1% by weight or even less, while others will form solutions having the specified viscosity only at a concentration approaching 10% by weight. These and other viscosities referred to herein can best be measured with a Brookfield Viscometer at 30 rpm. using a No. 1 spindle. Among the best of suitable gums are clarified locust bean gum, clarified guar gum, polyvinylalcohol, and dextran. The gum must be free from ionic or charged groups tending to cause electroendosmosis, and must be resistant to hydrolysis which might produce such ionic or charged groups; as pointed out above, polyacrylamide is excluded because of the electroendosmosis properties of commercially available polyacrylamide and because of the proclivity of this material to hydrolyze at various pH levels with the formation of carboxylate groups and/or an increase in electroendosmosis. In the case of natural products or natural gums such as locust bean gum and guar gum it is essential that the gum be in clarified form, free from hull fragments and other impurities which obscure or interfere with staining techniques used in isoelectric focusing.

The dry solid blend may contain from 2 to 99% by weight of purified agarose, the remainder consisting essentially of the water-soluble gum, and is preferably in finely-divided form. The greater the amount of electroendosmosis displayed by aqueous gels made from the purified agarose alone, the greater the amount of water-soluble gum needed in the blend; and the lower the concentration of an aqueous solution of the gum alone having the required viscosity, the less of the gum is required to produce a given decrease in the electroendosmosis properties of the aqueous gel made from the blend. In a preferred embodiment the dry blend consists essentially of finely divided particles of purified agarose mixed with particles of gum. Particle size is not critical and may be whatever is convenient for rapid dissolution in water, ranging from very coarse particles of the order of a millimeter or more in diameter down to as small as conveniently can be ground, of the order of those passing a 100 mesh screen.

Preferably the purified agarose employed has an electroendosmosis value ($-Mr$) no greater than 0.05, and the blend contains from 50 to 90% by weight of the purified agarose, the balance of 10 to 50% by weight being the desired water soluble gum.

The blend can be used by simply dissolving it in water by heating and stirring in the same manner as dissolving agarose alone. The ampholytes and/or buffers required in the gel for use in isoelectric focusing can be mixed with the dry solid blend or they can be separately dissolved before gelation occurs; they can also be added later after heating the gel to liquefy it and then allowing it to gel again. The amount of the blend used to produce the gel can be varied widely, depending upon the gel strength of porosity desired. The amount of agarose required to be dissolved in water to produce a gel of specified strength can vary considerably as a function of the source of the agarose and its previous history as well as its extent of purity. As a practical matter, the minimum strength for a gel useful as a medium for isoelectric focusing is about 100 $g/cm^2$. Since the gum component of the blend of the present invention does not affect gel strength of the purified agarose, it is the amount of agarose in the blend which is dissolved which controls the strength of the gel. In the case of certain commercially available agaroses the gel strength of a gel containing 1% by weight of agarose may be as much as 1000 to 1500 $g/cm^2$, while others display considerably lower strengths under the same conditions. Moreover, it is desirable as a practical matter that the hot solution of the blend in water have a viscosity sufficiently low so that the solution can readily be poured, i.e., a viscosity no greater than about 6000 cps. at 75° C. It is also important that sufficient gum component be present so that it forms, in the absence of agarose, a solution in water having a viscosity of at least 10 cps. at 25° C. Consequently, the amount of the blend of purified agarose with a water soluble gum employed in an aqueous gel in accordance with the present invention may vary from about 0.2% to 10% by weight of the water, preferably from 0.2 to 2% by weight. Gels containing from 0.2 to 2% of the blend based on the weight of the water are preferred because such gels have little or no molecular sieving effect regardless of the molecular weight or size of the protein subjected to isoelectric focusing, so that virtually all of the molecular separation which occurs in a function of the isoelectric point only of each protein. In addition, the preferred gels permit ready diffusion of the protein sample into the gel.

It is also possible to make such an aqueous gel free from electroendosmosis by dissolving the purified agarose and the gum individually in a single volume of water. That is, the gel can be made by dissolving in water at elevated temperature (1) purified agarose having an electroendosmosis ($-Mr$) value no greater than 0.10 and (2) a water-soluble gum free from hull fragments and other impurities interfering with staining, free from charged groups, and soluble by itself in boiling water without gelling to form a solution having a viscosity at a concentration no greater than 10% by weight of at least 10 cps. at 25° C., the amount of the total of said agarose and said gum being from 0.2 to 10% by weight of the water, the amount of agarose being from 2 to 99% by weight of said total, and the amount of said gum being sufficient to form, in the absence of said agarose, a solution in said water having a viscosity of at least 10 cps at 25° C., and allowing the solution to cool to form a gel.

The following specific examples will serve to illustrate the invention more fully without acting as a limitation upon its scope.

EXAMPLES

Agarose was separated from commercially available agar by the procedure of Blethen et al. U.S. Pat. No. 3,281,409 dated Oct. 25, 1966. A solution was then prepared by heating 12.0 grams of the agarose in 600 ml. of water while stirring. To the solution, after cooling to 60° C., were added 200 g of water-swollen and drained beads of a cation exchange resin, QAE Sephadex (Pharmacia), and the mixture was stirred for one-half hour at 60° C., and filtered; to the solution were added 2 liters of 80% aqueous isopropanol at 45° C. to coagulate the purified agarose which was separated on a screen dried at 50° C., and ground in a hammer mill to pass a 20-mesh screen. A portion of the purified agarose was dissolved in water by heating to 90° C. to form a solution containing 1% agarose by weight, cooled to cause it to gel, and its electroendosmosis ($-Mr$) found to be 0.03. The gel strength of a gel containing 1% by weight of the purified agarose was determined to be approximately 950 $g/cm^2$.

There was dispersed in 500 ml of distilled water 5 g of locust bean gum (powder), and the mix was heated to 100° C. and boiled for 30 seconds; 10 g of filter aid (Hyflo Supercell) was added to the resulting solution and the mixture was filtered at a pressure of 10–20 psi through a preheated filter bomb equipped with a suitable felt pad filter cloth. After filtration was complete, the filter cake was washed with 75 ml of distilled water, and the combined filtrate and washing was coagulated by mixing with 2.5 volumes of 85% isopropanol. After draining on a screen, the coagulum was resuspended in 85% isopropanol, allowed to stand for 15 minutes; drained and dried by heating at 60° C. for 4–6 hours, then ground in a hammer mill to 20–40 mesh (yield about 3–3.5 g). This clarified locust bean gum was water-soluble, free from charged or ionic groups, stable against hydrolysis which forms charged groups, and free from hulls and other impurities which accept stain and interfere with staining and/or detection of proteins in the gel; an aqueous solution containing 0.3% by weight of the gum by itself displayed a viscosity greater than 10 cps at 25° C.

A blend was prepared by mixing together 70 parts by weight of the purified finely divided agarose prepared as described above and 30 parts by weight of the finely divided particles of clarified locust bean gum. The blend was readily dissolved in water by stirring 0.5 gram into 100 ml of water and heating to the boiling point or until thoroughly dissolved; the solution was then cooled to 56° C. and 2% by weight of ampholytes was added with stirring. The solution was cast in a suitable form and allowed to gel by cooling, then stored at 4° C. for at least one hour before use.

The gel so prepared was found to have no measurable electroendosmosis and a gel strength of 350 $g/cm^2$. A sample of protein solution applied to the surface of the gel in the usual manner was effectively subjected to isoelectric focusing.

Similar results were obtained when there was substituted for the locust bean gum a sample of guar gum in the same amount.

When polyvinyl alcohol and dextran are used in place of clarified locust bean gum at concentrations which produce a viscosity greater than 10 cps at 25° C. (i.e. about 2–10%), then similar results are obtained.

We claim:

1. A dry solid composition capable of forming an aqueous gel free from electroendosmosis and suitable for use as a medium for isoelectric focusing, said composition consisting essentially of a blend of purified agarose having an electroendosmosis value ($-Mr$) less than 0.10 in an amount from 2 to 99% by weight and a gum soluble in boiling water without gelling, said gum being free from hull fragments and other impurities interfering with staining, free from charged groups and stable against hydrolysis which forms charged groups, and soluble by itself in water to form a solution of gum having a viscosity at a concentration no greater than 10% by weight of at least 10 cps at 25° C., said gum being clarified locust bean gum, clarified guar gum, polyvinyl alcohol or dextran.

2. An aqueous gel free from electroendosmosis having a gel strength of at least 100 $g/cm^2$ and suitable for use as a medium for isoelectric focusing consisting essentially of a gelled solution in water of the composition claimed in claim 1, the amount of said composition present being from 0.2 to 10% by weight of the water.

3. A composition as claimed in claim 1 in particulate form in which some particles consist of said purified agarose and the remaining particles consist of said gum.

4. A composition as claimed in claim 1 in which said agarose has an electroendosmosis value ($-Mr$) no greater than 0.05 and is present in an amount from 50 to 90% by weight.

5. A composition as claimed in claim 4 in particulate form in which some particles consist of said purified agarose and the remaining particles consist of said gum.

6. An aqueous gel free from electroendosmosis having a gel strength of at least 100 $g/cm^2$ and suitable for use as a medium for isoelectric focusing consisting essentially of a gelled solution in water of the composition claimed in claim 8, the amount of said composition present being from 0.2 to 10% by weight of the water.

7. An aqueous gel as claimed in claim 6 in which the amount of said composition is from 0.2 to 2% by weight of the water.

8. The method of making an aqueous gel free from electroendosmosis which comprises dissolving in water at elevated temperature (1) purified agarose having an electroendosmosis ($-Mr$) value no greater than 0.10 and (2) a water-soluble gum free from hull fragments and other impurities interfering with staining, free from charged groups, and soluble by itself in boiling water without gelling to form a solution having a viscosity at a concentration no greater than 10% by weight of at least 10 cps at 25° C., said gum being clarified locust bean gum, clarified guar gum, polyvinyl alcohol or dextran, the amount of the total of said agarose and said gum being from 0.2 to 10% by weight of the water, the amount of agarose being from 2 to 99% by weight of said total, and the amount of said gum being sufficient to form, in the absence of said agarose, a solution in said water having a viscosity of at least 10 cps at 25° C., and allowing the solution to cool to form a gel.

* * * * *

UNITED STATES PATENT AND TRADEMARK OFFICE
CERTIFICATE OF CORRECTION

PATENT NO. : 4,290,911

DATED : September 22, 1981

INVENTOR(S) : Richard B. Cook and Henry J. Witt

It is certified that error appears in the above—identified patent and that said Letters Patent is hereby corrected as shown below:

Column 6, line 45, "claim 8" should read --claim 4--.

Signed and Sealed this

First Day of December 1981

[SEAL]

Attest:

GERALD J. MOSSINGHOFF

Attesting Officer     Commissioner of Patents and Trademarks